(12) United States Patent
Narula et al.

(10) Patent No.: US 7,232,795 B2
(45) Date of Patent: Jun. 19, 2007

(54) DERIVATIVES OF DECAHYDRO-CYCLOPROP[E]INDENE COMPOUNDS AND THEIR USE IN PERFUME COMPOSITIONS

(75) Inventors: Anubhav P. S. Narula, Hazlet, NJ (US); Edward Mark Arruda, Cliffwood, NJ (US); Franc T. Schiet, Naarden (NL)

(73) Assignee: International Flavors & Fragrances Inc.

( * ) Notice: Subject to any disclaimer, the term of this patent is extended or adjusted under 35 U.S.C. 154(b) by 0 days.

(21) Appl. No.: 11/286,189

(22) Filed: Nov. 23, 2005

(65) Prior Publication Data

US 2007/0117727 A1    May 24, 2007

(51) Int. Cl.
*A61Q 13/00*    (2006.01)
*C07C 43/18*    (2006.01)

(52) U.S. Cl. ................. 512/19; 510/104; 568/665
(58) Field of Classification Search ............... 568/665; 512/19; 510/104
See application file for complete search history.

(56) References Cited

U.S. PATENT DOCUMENTS

| | | | |
|---|---|---|---|
| 2,330,979 A | 10/1943 | Krantz, Jr., et al. | |
| 2,424,029 A | 7/1947 | U.S.A., The Secretary of Agriculture | |
| 3,928,468 A * | 12/1975 | Billings et al. | 568/669 |
| 5,051,534 A | 9/1991 | Angelastro et al. | |

FOREIGN PATENT DOCUMENTS

| | | |
|---|---|---|
| SU | 1012908 | 4/1983 |
| WO | WO 00/18771 | 4/2000 |

OTHER PUBLICATIONS

Chen et al. (CAPLUS abstract, Chromatographia, vol. 23(7), 1987, pp. 502-506).*
Database Beilstein Database accession No. BRN 4229754 Tomilov, Y.V. et al.: Bull Acad. Sci. USSR Div. Chem. Sci. 38(12), 1989, p. 2513.
Database Beilstein Database accession No. BRN 3042950 Furukawa, J. et al.: Tetrahedron 24, 1968, p. 53-58.
Database Beilstein Database accession No. BRN 4229730 Imai, T. et al.: J. Org. Chem. 55(17), 1990, pp. 4986-4988.
Database Beilstein Database accession No. BRN 2049817 Shono, T. et al.: J. Org. Chem. 35(12), 1970, pp. 4157-4160.
Database Beilstein Database accession No. BRN 9636333 Lam, P. Y. S. et al.: Tetrahedron Lett. 44(26), 2003, pp. 4927-4932.
Database Beilstein Database accession No. BRN 9551934 Zhang, J.L. et al.: Tetrahedron Lett. 44(48), 2003, pp. 8733-8738.
Database Beilstein Database accession No. BRN 8038172 Sugawara, M. et al.: Syn. Lett. 10, 1998, pp. 1057-1058.
Database Beilstein Database accession No. BRN 2433084 Lishanskii et al.: Dokl. Chem. 179, 1968, p. 309.
Database Beilstein Database accession No. BRN 2553721 Schoellkopf, U. et al.: Chem. Ber. 98, 1965, pp. 2221-2235.
Database Beilstein Database accession No. BRN 4840033 and 4840010 Meijere, A.D. et al.: Synthesis 7, 1991, pp. 547-559.
Database Beilstein Database accession No. Brn 6593554 Militzer, H.C. et al.: Synthesis 10, 1993, pp. 998-1012.
European Patent Office Search Report, Mar. 2007.

* cited by examiner

*Primary Examiner*—Rosalynd Keys
(74) *Attorney, Agent, or Firm*—Elizabeth M. Quirk

(57) ABSTRACT

The present invention is directed to novel substituted cyclopropane ethers compounds of the general formulae selected from the group consisting of

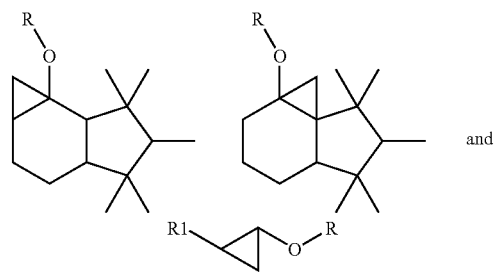

and R and R1 independently represent a hydrogen or a straight, branched, or cyclic hydrocarbon moiety consisting of less then 15 carbon atoms and containing single and/or double bonds.

11 Claims, No Drawings

DERIVATIVES OF DECAHYDRO-CYCLOPROP[E]INDENE COMPOUNDS AND THEIR USE IN PERFUME COMPOSITIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allows perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the novel decahydro-cycloprop[e]indene compounds, represented by the general structures of Formulae I–III set forth below:

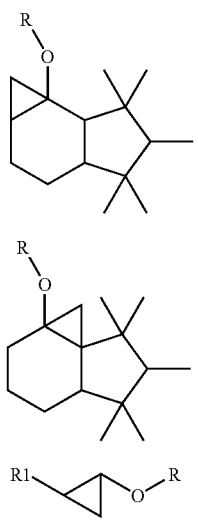

Formula I

Formula II

Formula III wherein R and R1 independently represent a hydrogen or a straight, branched, or cyclic hydrocarbon moiety consisting of less then 15, preferably less then 10, most preferably less then 7 carbon atoms and containing single and/or double bonds.

Another embodiment of the invention is a method for enhancing a perfume composition by incorporating an olfactory acceptable amount of the compounds provided above.

These and other embodiments of the present invention will be apparent by reading the following specification.

DETAILED DESCRIPTION OF THE INVENTION

In Formulae I, II and III above, R and R1 independently represent a hydrogen or a straight, branched, or cyclic hydrocarbon moiety consisting of less then 15, preferably less then 10, most preferably less then 7 carbon atoms and containing single and/or double bonds. Suitable straight hydrocarbon moieties include ethyl, propyl, butyl, pentyl, hexyl, and the like. Suitable branched hydrocarbon moieties include isopropyl, sec-butyl, tert-butyl, 2-ethyl-propyl, and the like. Suitable cyclic hydrocarbon moieties include cyclopropane, cyclobutane, cyclopentane, cyclopentene, 1,4-cyclopentene, cyclohexane, cyclohexene and the like. Suitable hydrocarbon moieties containing double bonds include ethene, propene, 1-butene, 2-butene, penta-1-3-deine, hepta-1,3,5-triene and the like.

In the preferred embodiment of the invention, the novel compounds of the present invention are represented by the following structures:

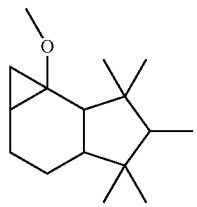

Formula IV

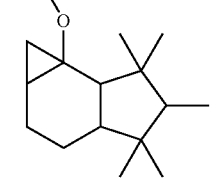

Formula V

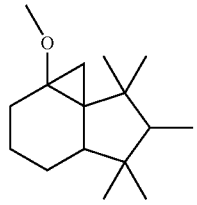

Formula VI

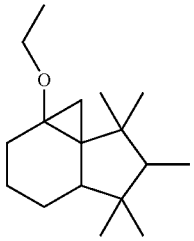

Formula VII

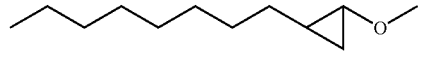

Formula VIII

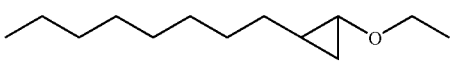

Formula IX

Those with the skill in the art will appreciate that the compound of Formula IV is 6b-methoxy-4,4,5,6,6,-pentamethyl-decahydro-cyclopropa[e]indene; the compound of Formula V is 6b-ethoxy-4,4,5,6,6,-pentamethyl-decahydro-cyclopropa[e]indene; the compound of Formula VI is 1a-methoxy-5,5,6,7,7-pentamethyl-octahydro-cyclopropa[d]indene; the compound of Formula VII is 1a-ethoxy-5,5,6,7,7-pentamethyl-octahydro-cyclopropa[d]indene; the compound of Formula VIII is 1-methoxy-2-octyl-cyclopropane and the compound of Formula IX is 1-ethoxy-2-octyl-cyclopropane.

The table below lists additional compounds derived from Formula I that are described in the present invention:

| R | Compound |
|---|---|
| (CH$_2$)$_2$CH$_3$ | 6b-propoxy-4,4,5,6,6,-pentamethyl-decahydro-cyclopropa[e]indene |
| (CH$_2$)$_4$CH$_3$ | 6b-pentyloxy-4,4,5,6,6,-pentamethyl-decahydro-cyclopropa[e]indene |
| CHCH(CH$_2$)$_3$CH$_3$ | 6b-hex-1-enyloxy-4,4,5,6,6,-pentamethyl-decahydro-cyclopropa[e]indene |
| CH(CH$_3$)$_2$ | 6b-isopropoxy-4,4,5,6,6,-pentamethyl-decahydro-cyclopropa[e]indene |
| C(CH$_3$)$_3$ | 6b-tert-butoxy-4,4,5,6,6,-pentamethyl-decahydro-cyclopropa[e]indene |
| CHCH$_2$ | 6b-vinyloxy-4,4,5,6,6,-pentamethyl-decahydro-cyclopropa[e]indene |
|  | 6b-cyclopentyloxy-4,4,5,6,6,-pentamethyl-decahydro-cyclopropa[e]indene |
|  | 6b-cyclohexyloxy-4,4,5,6,6,-pentamethyl-decahydro-cyclopropa[e]indene |
|  | 6b-(cyclohex-2-enyloxy)-4,4,5,6,6,-pentamethyl-decahydro-cyclopropa[e]indene |
|  | 6b-cyclopentyloxy-4,4,5,6,6,-pentamethyl-decahydro-cyclopropa[e]indene |

The table below lists additional compounds derived from Formula II that are described in the present invention:

| R | R1 | Compound |
|---|---|---|
| CH$_3$CHCH$_2$CH$_3$ | CH$_3$ | 1-sec-butyl-2-methoxy-cyclopropane |
| CHC(CH$_3$)$_3$ | CH$_3$ | 1-(2,2-dimethyl-propyl)-2-methoxy-cyclopropane |
| CH$_3$(CH)$_2$(CH$_2$)$_4$CH$_3$ | CH$_3$ | 1-methoxy-2-oct-2-enyl-cyclopropane |
| (CH$_2$)$_6$CH | CH$_3$ | 1-methoxy-2-oct-7-ynyl-cyclopropane |
| (CH$_2$)$_7$CH$_3$ | CH$_2$CH$_3$ | 1-ethoxy-2-octyl-cyclopropane |
| (CH$_2$)$_2$CH$_3$ | (CH$_2$)$_2$CH$_3$ | 1-propoxy-2-propyl-cyclopropane |
| (CH$_2$)$_7$CH$_3$ | (CH$_2$)$_7$CH$_3$ | 1-octyl-2-octyloxy-cyclopropane |
| 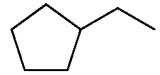 | CH$_3$ | [2-(2-methoxy-cyclopropyl)-ethyl]-cyclopentane |

| R | R1 | Compound |
|---|---|---|
| 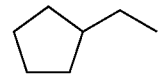 | (CH$_2$)$_3$CH$_3$ | [2-(2-butoxy-cyclopropyl)-ethyl]-cyclopentane |
| 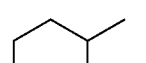 | CH$_3$ | (2-methoxy-cyclopropylmethyl)-cyclohexane |
| 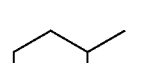 | CH$_2$CH$_3$ | (2-ethoxy-cyclopropylmethyl)-cyclohexane |

The compounds of the present invention may be prepared from the corresponding compounds containing a double bond by Simmon-Smith reaction of the following sequences:

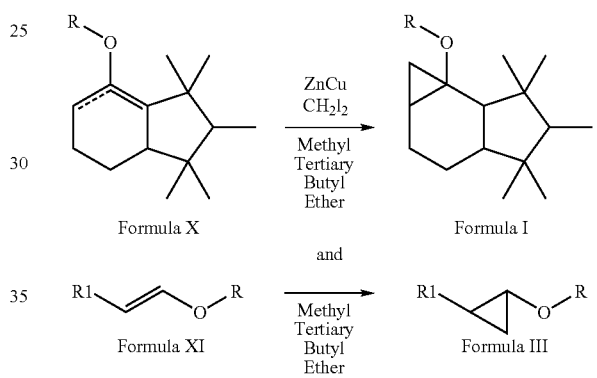

The alkenes used in the above reaction to prepare the compounds of the present invention are disclosed in U.S. Pat. Nos. 5,665,698 and 5,733,866. Two of the possible precursors of the compounds of the present invention are 1-methoxy-1-decene and 1-ethoxy-1-decene.

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as High Performance Liquid Chromatography ("HPLC"), and particularly gel chromatography and solid phase microextraction ("SPME").

We have discovered that the compounds of Formulae IV–VII have warm, woody, cashmeran, ambery, nitro musk notes and compounds of Formulae VIII and IX display an aldehydic, fresh citrus note that are well suited for use as a fragrance ingredient.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams. All U.S. patents mentioned above are incorporated herein by reference. IFF as used in the examples is understood to mean International Flavors & Fragrances Inc., New York, N.Y., USA. All fragrance materials mentioned in the examples are available from IFF.

EXAMPLE A

Preparation of 6b-methoxy-4,4,5,6,6,-pentamethyl-decahydro-cyclopropa[e]indene

To a dry 500 ml multi-neck round bottom flask fitted with an air stirrer, nitrogen inlet condenser and an addition funnel 8 g of ZnCu, 70 ml of Methyl Tertiary Butyl Ether (MTBE) and 3 crystals of $I_2$ were added and stirred. 23 g of $CH_2I_2$ was added while stirring. A heating source was applied to the mixture. 22 g of 7-methoxy-1,1,2,3,3-pentamethyl-2,3,3a,4,5,7a-hexahydro-1H-indne was added drop-wise over 20 minutes. The mixture was aged for 7.5 hours. The mixture was quenched with saturated $NH_4Cl$, aqueous layer separated and the organic layer washed with 200 ml of water. The organic layer was then dried over anhydrous $MgSO_4$.

The NMR of the 6b-methoxy-4,4,5,6,6,-pentamethyl-decahydro-cyclopropa[e]indene is as follows: 0.6 ppm (m, 4H); 0.7 ppm (m, 1H); 0.8 ppm (s, 3H); 0.9 ppm (s, 4H); 1.0 ppm (s, 2H); 1.1 ppm (s, 7H); 1.2 ppm (m, 2H); 1.2 ppm (m, 1H); 1.3 ppm (m, 1H); 2.1 ppm (d, 1H); 2.2 ppm (m, 1H); 3.3 ppm (s, 3H).

EXAMPLE B

Preparation of 6b-ethoxy-4,4,5,6,6,-pentamethyl-decahydro-cyclopropa[e]indene

To a dry 200 ml multi-neck round bottom flask fitted with an air stirrer, nitrogen inlet condenser and an addition funnel 1 g of ZnCu, 30 ml of Methyl Tertiary Butyl Ether (MTBE) and 1 crystal of $I_2$ were added and stirred. 3.3 g of $CH_2I_2$ was via syringe. The mixture was heated maintained at 60° C. 1.97 g of 7-ethoxy-1,1,2,3,3-pentamethyl-2,3,3a,4,5,7a-hexahydro-1H-indne was added in one portion. The mixture was aged for 7.5 hours. The mixture was quenched with saturated $NH_4Cl$, aqueous layer separated and the organic layer washed with 200 ml of water. The organic layer was then dried over anhydrous $MgSO_4$.

The NMR of the 6b-ethoxy-4,4,5,6,6,-pentamethyl-decahydro-cyclopropa[e]indene is as follows: 0.2 ppm (s, 1H); 0.8 ppm (m, 10H); 1.0 ppm (d, 8H); 1.2 ppm (m, 3H); 1.3 ppm (m, 1H); 1.5 ppm (m, 2H); 1.6 ppm (s, 2H); 1.6–1.7 ppm (m, 1H); 1.8 ppm (d, 1H); 2.3 ppm (d, 1H); 3.3 ppm (m, 1H); 3.7 ppm (m, 1H).

EXAMPLE C

Preparation of 1-methoxy-2-octyl-cyclopropane

To a dry 200 ml multi-neck round bottom flask fitted with an air stirrer, nitrogen inlet condenser and an addition funnel 100 ml of diethyl Ether, 7.5 g of ZnCu and 27 g of g of $CH_2I_2$ were added, stirred and heated to reflux. 3.3 was via syringe. The mixture was heated maintained at 60° C. In 30 minutes 170 g 1-methoxy-1-decene was added dropwise via the addition funnel. A crystal of $I_2$ was added and the mixture was aged overnight. The mixture was quenched with saturated $NH_4Cl$, aqueous layer separated and the organic layer washed with 200 ml of water. The organic layer was then dried over anhydrous $MgSO_4$.

The NMR of the 1-methoxy-2-octyl-cyclopropane is as follows: 0.1 ppm (s, 1H); 0.2 ppm (m, 1H); 0.6 ppm (m, 1H);

0.7 ppm (m, 1H); 0.8 ppm (m, 1H); 0.9 ppm (s, 3H); 1.1 ppm (m, 1H); 1.3 ppm (s, 8H); 1.4 ppm (m, 2H); 2.9 ppm (s, 1H); 3.2 ppm (s, 1H); 3.3 ppm (s, 1H); 3.4 ppm (s, 1H).

EXAMPLE D

Preparation of 1-ethoxy-2-octyl-cyclopropane

To a dry 200 ml multi-neck round bottom flask fitted with an air stirrer, nitrogen inlet condenser and an addition funnel 10 ml of diethyl Ether, 2 g of ZnCu and 1 crystal of $I_2$ were added and stirred for 5 minutes. 3.3 g of g of $CH_2I_2$ were added to the mixture and the mixture was heated to 60° C. In 30 minutes 2 g 1-ethoxy-1-decene was added in one portion. The mixture was aged overnight. The mixture was quenched with saturated $NH_4Cl$, aqueous layer separated and the organic layer washed with 2 100 ml portions of water. The organic layer was then dried over anhydrous $MgSO_4$.

The NMR of the 1-ethoxy-2-octyl-cyclopropane is as follows: 0.1 ppm (s, 1H); 0.2 ppm (m, 1H); 0.6 ppm (m, 1H); 0.7 ppm (s, 1H); 0.8 ppm (s, 1H); 0.9 ppm (s, 3H); 1.1 ppm (m, 4H); 1.3 ppm (s, 11H); 1.4 ppm (m, 2H); 2.9 ppm (s, 1H); 3.2 ppm (s, 1H); 3.6 ppm (s, 2H).

EXAMPLE E

Incorporation of 6b-methoxy-4,4,5,6,6,-pentamethyl-decahydro-cyclopropa[e]indene into a Fragrance Formulation A fragrance was prepared according to the following formulation:

| | |
|---|---:|
| 4h-Pyran-4-One, 2-Ethyl-3-Hydroxy 10% | 3.00 |
| Aldehyde AA Triplal | 3.00 |
| Anisaldehyde para | 25.00 |
| Benzyl Acetate | 20.00 |
| Benzyl Salicylate | 35.00 |
| Cyclamal | 30.00 |
| 6b-methoxy-4,4,5,6,6,-pentamethyl-decahydro-cyclopropa-[e]indene | 25.00 |
| Dihydro Methyl Jasmonate | 100.00 |
| Ethyl Vanillin 10% | 4.00 |
| Galaxolide | 175.00 |
| Geraniol | 100.00 |
| Helional | 45.00 |
| Hexenyl Acetate, Cis-3 | 3.00 |
| Hexenyl Salicylate, Cis-3 | 40.00 |
| Hexyl Salicylate | 15.00 |
| Hydrocinnamaldehyde, Para Tertiary Butyl Alpha Methyl | 90.00 |
| Hydroxycitronellal | 35.00 |
| Nerol | 70.00 |
| Phenyl Ethyl Alcohol | 150.00 |
| Piperonal | 15.00 |
| Terpineol | 15.00 |
| Undecalactone Gamma | 2.00 |
| Total weight | 1000.00 |

This fragrance was described as having warm, woody, cashmeran, ambery odor notes.

EXAMPLE F

Incorporation of 6b-ethoxy-4,4,5,6,6,-pentamethyl-decahydro-cyclopropa[e]indene into a Fragrance Formulation A fragrance was prepared according to the following formulation:

| | |
|---|---:|
| 2-Adamantanol, 4-Methyl-8-Methylene | 200.00 |
| Aldehyde AA Triplal | 3.00 |
| Cardamom Oil Ceylon LMR | 5.00 |
| 6b-ethoxy-4,4,5,6,6,-pentamethyl-decahydro-cyclopropa[e]inden | 17.00 |
| Dihydro Methyl Jasmonate | 115.00 |
| Galaxolide | 75.00 |
| Iso E Super | 225.00 |
| Koavone | 175.00 |
| Linalool | 35.00 |
| Linalyl Acetate | 35.00 |
| Lyral | 25.00 |
| Methyl Ionone Gamma | 45.00 |
| Pepper Oil Black | 5.00 |
| Thyme Oil White LMR | 3.00 |
| Tobacco Leaf Absolute | 2.00 |
| Tonalid | 35.00 |
| Total weight | 1000.00 |

This fragrance was described as having warm, woody, cashmeran, ambery odor notes.

EXAMPLE G

Incorporation of 1-methoxy-2-octyl-cyclopropane into a Fragrance Formulation

A fragrance was prepared according to the following formulation:

| | |
|---|---:|
| Acetaldehyde DEA10% DPG | 15 |
| l-methoxy-2-octyl-cyclopropane | 12 |
| Calone | 10 |
| Cyclamal Extra | 22 |
| Eth Buty "F&F" | 6.6 |
| Eth Meth Phen Glyc | 10 |
| Eth-2-Meth Buty | 5 |
| Hexenol, beta, gamma, Cis 10%DPG | 170 |
| Hexenyl Iso Buty, cis-3 10% DPG | 8.5 |
| Iso Amy Acet | 10 |
| Iso Amyl Buty | 45 |
| Lemon Terpenes Dist "PFG" | 50 |
| Lilal | 52 |
| Linalyl Acet | 0.8 |
| Linalyl Iso Buty "F&F" | 14 |
| Melonal Giv 10% DPG | 60 |
| Nona Dienol, 2-trans-6 US 1% DEP | 10 |
| Oxyphenylon | 3 |
| Phenyl Eth Alc White Extra | 2 |
| Pineapple Comp 1% DPG | 3.8 |
| Prenyl Acetate | 0.5 |
| Scentenal 10% DPG | 3 |
| Terpineol, Alpha | 0.8 |
| Undecalactone, Gamma | 10 |
| Vanillin | 3 |
| DIPG | 273 |
| Total weight | 800 |

This fragrance was described as having aldehydic and fresh citrus odor notes.

EXAMPLE G

Incorporation of 1-ethoxy-2-octyl-cyclopropane into a Fragrance Formulation

A fragrance was prepared according to the following formulation:

| | |
|---|---|
| Acetaldehyde DEA10% DPG | 15 |
| Cyclopropanated 1-ethoxy-1-decene | 12 |
| Calone | 10 |
| Cyclamal Extra | 22 |
| Eth Buty "F&F" | 6.6 |
| Eth Meth Phen Glyc | 10 |
| Eth-2-Meth Buty | 5 |
| Hexenol, beta, gamma, Cis 10%DPG | 170 |
| Hexenyl Iso Buty, cis-3 10% DPG | 8.5 |
| Iso Amy Acet | 10 |
| Iso Amyl Buty | 45 |
| Lemon Terpenes Dist "PFG" | 50 |
| Lilal | 52 |
| Linalyl Acet | 0.8 |
| Linalyl Iso Buty "F&F" | 14 |
| Melonal Giv 10% DPG | 60 |
| Nona Dienol, 2-trans-6 US 1% DEP | 10 |
| Oxyphenylon | 3 |
| Phenyl Eth Alc White Extra | 2 |
| Pineapple Comp 1% DPG | 3.8 |
| Prenyl Acetate | 0.5 |
| Scentenal 10% DPG | 3 |
| Terpineol, Alpha | 0.8 |
| Undecalactone, Gamma | 10 |
| Vanillin | 3 |
| DIPG | 273 |
| Total weight | 800.00 |

This fragrance was described as having aldehydic and fresh citrus odor notes.

What is claimed is:

1. A compound of formula selected from the group consisting of

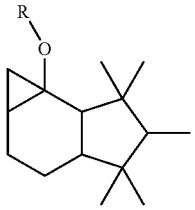 and 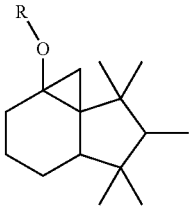

wherein R is a hydrogen or a straight, branched, or cyclic hydrocarbon moiety consisting of less then 15 carbon atoms and containing single and/or double bonds.

2. A compound of claim 1, wherein R is a hydrocarbon moiety consisting of less then 10 carbon atoms.

3. A compound of claim 1, wherein R is a hydrocarbon moiety consisting of less then 7 carbon atoms.

4. A method of improving, enhancing or modifying a fragrance formulation through the addition of an olfactory acceptable amount of the compound of claim 1.

5. The method of claim 4 wherein the fragrance is incorporated into a product selected from perfumes, colognes, toilet waters, cosmetic products, personal care products, fabric care products, cleaning products and air fresheners.

6. The method of claim 5 wherein the cleaning product is selected from the group consisting of detergents, dishwashing compositions, scrubbing compounds and window cleaners.

7. The method of claim 4, wherein the amount incorporated into a fragrance is from about 0.005 to about 10 weight percent.

8. The method of claim 4, wherein the amount incorporated into a fragrance is from about 0.5 to about 8 weight percent.

9. The method of claim 4, wherein the amount of incorporated into a fragrance is from about 1 to about 7 weight percent.

10. A fragrance formulation containing an olfactory effective amount of the compound of claim 1.

11. A fragrance product containing a compound of claim 1.

* * * * *